(12) United States Patent
Schneider et al.

(10) Patent No.: US 6,329,160 B1
(45) Date of Patent: Dec. 11, 2001

(54) BIOSENSORS

(75) Inventors: Rene Schneider, Microbiology; Tony Vancov, Euguna, both of (AU); Karen Jury, Norwich (GB)

(73) Assignee: CRC for Waste Management and Pollution Control Limited, Kensington (AU)

(*) Notice: Subject to any disclaimer, the term of this patent is extended or adjusted under 35 U.S.C. 154(b) by 0 days.

(21) Appl. No.: 09/230,288
(22) PCT Filed: Jul. 25, 1997
(86) PCT No.: PCT/AU97/00473
§ 371 Date: Sep. 7, 1999
§ 102(e) Date: Sep. 7, 1999
(87) PCT Pub. No.: WO98/04716
PCT Pub. Date: Feb. 5, 1998

(30) Foreign Application Priority Data

Jul. 29, 1996 (AU) .................................... PO 1280

(51) Int. Cl.$^7$ .......................... G01N 33/53; G01N 33/569
(52) U.S. Cl. .............................. 435/7.31; 435/4; 435/7.6; 435/7.23; 435/8; 435/189; 435/287.1; 435/252.33; 435/325; 435/7.32; 435/7.37; 536/23.2; 536/24.1
(58) Field of Search ................... 435/4, 7.6, 7.23, 435/8, 189, 787.1, 288.1, 291.1, 252.33, 325, 7.35, 7.32, 7.37; 536/232.2, 24.1

(56) References Cited

U.S. PATENT DOCUMENTS 5,256,568 * 10/1993 Panayotatos .................... 435/252.33
5,571,722 * 11/1996 Rosson .............................. 435/320.1

FOREIGN PATENT DOCUMENTS

0649905 A1 * 10/1994 (EP) .............................. C12N/15/53
0649905 4/1995 (EP) .
WO 92/15687 * 9/1992 (WO) ............................. C12N/15/31
9804716 2/1998 (WO) .

OTHER PUBLICATIONS

Van Dyk et al. (1994). Rapid and sensitive polutant detection by induction of heat shock gene–bioluminescence gene fusion. Appl. Environ. Microbiol. 60:1414–1420.*

Perez–Martin et al. (1995). Integration host factor suppresses promiscuous activation of the s54–dependent promoter Pu of Psudomonas putida. PNAS USA. 92:7277–7281.*

Delgado et al. (1994). Gengetic evidence for activation of the positive transcriptional regulator XyIR, a member of the NtrC family of regulators, by effector binding. J Biol. Chem. 269(11):8059–8062.*

Robinson (1991). Capturing the light and capturing the market. TIBTECH. 9:72–76.*

Meighen (1993). Bacterial bioluminescence: organization, regulation, and application of the lux genes. FASEB Journal. 7:1016–1022.*

(List continued on next page.)

Primary Examiner—Long V. Le
Assistant Examiner—Minh-Quan K. Pham
(74) Attorney, Agent, or Firm—Browdy and Neimark

(57) ABSTRACT

A genetic construct for use in a biosensor comprising: (a) a first nucleic acid molecule including a sequence encoding a reporter molecule having a detectable activity; and (b) a second nucleic acid molecule including a sequence encoding an enzyme which produces a substrate for the reporter molecule, the first sequence being under the control of a first inducible promoter and the second sequence being under the control of a second inducible promoter. A biosensor for measuring an environmental signal comprising a cell including the genetic construct and a means for measuring the activity of the reporter molecule in the cell when the cell has been exposed to the environmental signal.

20 Claims, 8 Drawing Sheets

OTHER PUBLICATIONS

Meighen (1991). Molecular biology of bacterial bioluminescence. Microbiol. Rev. 55(1):123–142.*

Burlage et al., "Living Biosensors for the Management and Manipulation of Microbial Consortia", *Microbio.* 48:291–309, (1994).

Van Dyk et al., "Rapid and Sensiive Pollutant Detection by Induction of Hear Shock Gene–Bioluminescene Gene Fusion", *Applied and Environmental Microbio.*, 60:1414–1420, (1994).

* cited by examiner

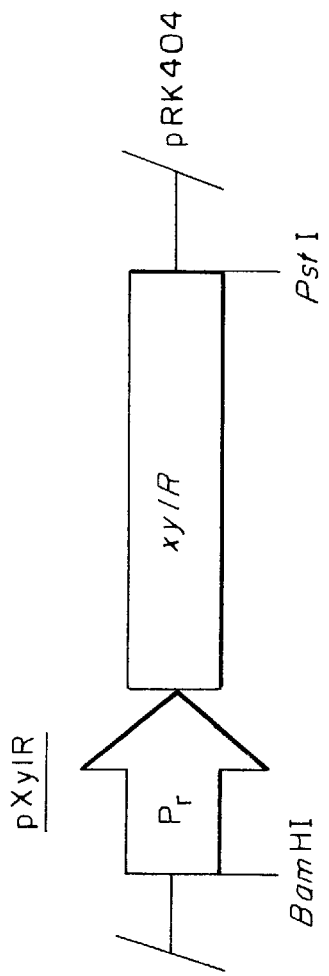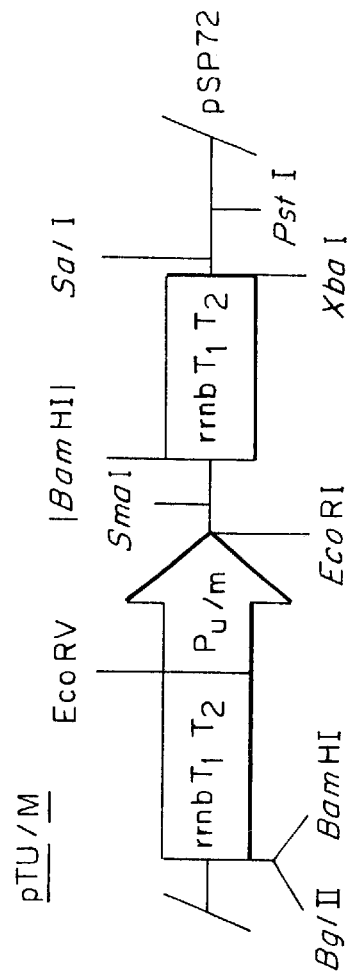
FIG. 7
FIG. 8

PLASMID NAME: pLEU

PLASMID SIZE: 9.80 kb

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

CCAATGCATT GTGGATCATC CCGATAAAAA          30

(2) INFORMATION FOR SEQ ID NO: 2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

CGGGATCCCG CCCGTTTTCA CACAACCT          28

(2) INFORMATION FOR SEQ ID NO: 3:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

CGGGATCCCG GATCTGCGTT GAGGTGGAT          29

(2) INFORMATION FOR SEQ ID NO: 4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

CCAATGCATT GCCCGTTTTC ACACAACCT                            29

(2) INFORMATION FOR SEQ ID NO: 5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

GAAGATCTTC GGGATCCTCA GAAGTGAAAC GCCGTA                    36

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

CGGATATCCT GATGCAAAAA CGAGGCT                              27

(2) INFORMATION FOR SEQ ID NO: 7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

GAAGATCTCA GAAGTGAAAC GCCGTA                               26

(2) INFORMATION FOR SEQ ID NO: 8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GCTCTAGAGC CTGATGCAAA AACGAGGTC                            29

(2) INFORMATION FOR SEQ ID NO: 9:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GGAATTCCCC CCGATTAAAT GGATGGC                                           27

(2) INFORMATION FOR SEQ ID NO: 10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GGGGTACCCC GCAAAAAGTT TCCAAATTTC AT                                     32

(2) INFORMATION FOR SEQ ID NO: 11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

CGGAATTCCG AAGGACTCTC TATGAAATTT GG                                     32

(2) INFORMATION FOR SEQ ID NO: 12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

CCTCGCTGCA ACTCGAAAT                                                    19

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GGGGTACCCC CTTGAGGAGT AAAACAGGTA TG                                     32

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear

```
        (ii) MOLECULE TYPE: cDNA (xi) SEQUENCE DESCRIPTION: SEQ ID NO: 14:

GCAAGGGATC CACTTACAAT TAGGCAAAGG                                              30

(2) INFORMATION FOR SEQ ID NO: 15:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO: 15:

GTTGGAATTC CCCCCGATTA AATGG                                                   25

(2) INFORMATION FOR SEQ ID NO: 16:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO: 16:

GCAAGGGATC CACTTACAAT TAGGCAAAGG                                              30

(2) INFORMATION FOR SEQ ID NO: 17:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO: 17:

GGAAAGCGCG ATGAACCTT                                                          19

(2) INFORMATION FOR SEQ ID NO: 18:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO: 18:

GCGAATTCCT GAAGGGTCAC CACTATTT                                                28
```

BIOSENSORS

TECHNICAL FIELD

The invention relates to the use of biosensors for detecting environmental signals based on the measurement of genetic responses of cells to those signals.

BACKGROUND ART

The standard approach for biosensor measurements "based on genetic responses" is to attach reporter genes to the relevant promoters and to measure the signal (which consists of the activity of the enzyme encoded by the reporter gene) in response to the analyte of interest. The first publication dealing with the use of the bacterial luciferase operon to achieve such measurements appeared in 1984 (Baldwin et al., 1984). Since that time many more publications detailing the use of this reporter to probe the activity of promoters have appeared. Today there are probably several thousand publications on this subject. Most of these publications rely on the use of luxAB fusions or of entire lux cassettes. The more restricted goal of measuring the concentration of pollutants with such constructs was first proposed and demonstrated by Gary Sayler's group at the University of Tennessee in the USA (King et al., 1990). Burlage & Kuo (1994) recently reviewed the application of such biosensors with respect to environmental monitoring applications.

Practically all of the constructs described utilise either the entire lux operon for activity measurement or the luciferase part of it (lux AB, in this case the activity is measured by external addition of the aldehyde substrate). The major disadvantage of using the entire lux operon is that production of the enzyme responsible for generating the substrate of luciferase (the fatty acid reductase encoded by lux CDE) occurs simultaneously with the synthesis of luciferase. It is therefore probable that the amount of substrate produced by the cell will be insufficient for saturation of luciferase. The present inventors have introduced modifications into constructs suitable for biosensors in an attempt to address this disadvantage thereby allowing maximal light output as soon as luciferase is synthesised.

DISCLOSURE OF THE INVENTION

In a first aspect, the present invention consists in a genetic construct for use in a biosensor comprising:

(a) a first nucleic acid molecule including a sequence encoding a reporter molecule having a detectable activity; and (b) a second nucleic acid molecule including a sequence encoding an enzyme which produces a substrate for the reporter molecule, the first sequence being under the control of a first inducible promoter and the second sequence being under the control of a second inducible promoter.

In a preferred embodiment, the first nucleic acid molecule encodes bacterial luciferase Lux AB or a functional equivalent thereof and the second nucleic acid molecule encodes Lux CDE enzyme fatty acid reductase or a functional equivalent thereof. These genes may be obtained from any of the lux operons of bioluminescent microorganisms, most of which belong to the genera Vibrio, Xenorhabdus, Photorhabdus and Photobacterium (Meighen, 1994). The detectible activity in this system is the generation of light.

It will be appreciated that any inducible promoters will be suitable for the present invention. Examples of some promoters that are suitable are listed in Appendix 2. This list, however, is not an exhaustive list but is provided to demonstrate the large number of possible promoters. The choice of the first promoter is often dependent on the environmental signal to which the biosensor is adapted to react. In particular, when the biosensor is used to detect xylene, the Pu promoter is especially suitable as the first promoter.

A further preferred embodiment of the first aspect of the present invention is the genetic construct adapted for the detection of xylene set out in FIG. 14.

The distinct advantage of the genetic construct of the present invention is that when in a cell, expression of the enzyme can be induced separately from the expression of the reporter molecule. This allows the cell to be loaded with substrate produced by the enzyme. The substrate is immediately available for use by the reporter molecule when it is produced, thereby giving a quick response to the signal detected. When the reporter molecule is made in response to an environmental signal, it can react maximally to give a detectable activity. Preferably the first promoter is inducible by exposure to an environmental signal to be tested. Induction can be achieved directly by the signal or indirectly by activating one or more separate pathways in the cell containing the construct.

The genetic construct can include further nucleic acid molecules encoding auxiliary element or elements required for activation of the reporter molecule via its promoter. Examples is include regulatory genes or nucleic acid molecules expressing "second message" molecules to activate the first promoter.

The effector specificities of existing promoters which depend on an indirect activation pathway by regulatory genes can be altered by mutation of the signal binding site of the regulatory protein (Ramos et al., *Proc. Natl. Acad. Sci. USA*, 83, 8467–8471, 1986). New promoters can be identified using promoterless promoter-probe vectors based on transposons such as those described by deLorenzo et al. (deLorenzo, V.; Herrero, M.; Jakubzik, U. & Timmis, K. N. *J. Bact.*, 172, 6568–6572, 1990) or Sohaskey et al. (Sohaskey, C. D.; Im, H. & Schauer, A. T., *J. Bact.*, 1674, 367–376, 1992).

In a second aspect, the present invention consists in a biosensor for measuring an environmental signal comprising a cell including the genetic construct of the first aspect of the present invention and a means for measuring the activity of the reporter molecule in the cell when the cell has been exposed to the environmental signal.

The cell can be any cell including bacterial, yeast, fungal and other plant cells and animal. Preferably the cell is a bacterial cell. The environmental signal can be pollutants, toxins, temperature, irradiation, biological, and chemical.

When the bacterial luciferase system is used, the basic genetic units of the sensor are the second nucleic acid molecule encoding the production of the fatty acid reductase (unit 2), the first nucleic acid molecule encoding the reporter element containing the luciferase genes and the first promoter (unit 1) as well as in some instances a third unit which would supply auxiliary elements for activation of the sensor element such as regulatory genes (unit 3). In commercial sensors all elements would be ideally inserted in the chromosome of the host organism. Alternatively, all units may be placed on plasmids, or a combination of chromosomally inserted elements and plasmid-borne constructs may be used. For example, where three units are used, unit 2 and unit 3 may be inserted in the chromosome whilst unit 1 is located on a plasmid.

A functional biosensor unit using the bacterial luciferase system consists of a device where the sample to be tested is contacted with biosensor cells which include a genetic construct according to the first aspect of the present invention (in a cuvette for example) and an instrument capable of measuring the light output of the cells. Any light measuring device would in principle be applicable, but the most appropriate systems are photomultipliers, charge coupled devices, luminometers, photometers, fiber-optic cables or liquid scintillation counters. These systems can be portable or laboratory based, they can be adapted for single analysis or high throughput devices for multiple analyses. A survey of more than 90 commercially available systems suitable for the present invention has been published by Stanley in J. Bioluminesc. Chemiluminescence, 7, 77–108, 1992 and regular updates have appeared since.

Analytes can be measured by the biosensor when adsorbed to surfaces, dissolved in liquid media or when present in the gasphase. Condition for measurement is that sufficient moisture be available to ensure the function of the biosensor cells which include a genetic construct. Ideally, samples are diluted with a buffer of appropriate composition prior to analysis and incubated in this solution. Alternatively, analytes of interest may be separated from the sample prior to analysis using means such as solvents or selectively permeable barriers such as membranes. Analytes may also be concentrated prior to analysis by, for example, passing a gas sample through a liquid or through a suitable solid adsorbent.

The biosensors can be used to detect organic or inorganic chemical or environmental signal which elicits a genetic response in an organism. Microbial systems are targeted primarily, but mammalian, plant or fungal promoters can also be used. In addition, the biosensors can be used to detect physiological responses such as starvation, toxicity or sporulation by inserting the luciferase genes behind promoters suitable for physiological measurements. The biosensors can be used to detect pollutants attached to particles, dissolved in aquatic samples or dispersed in the gas phase. The measurements usually need, however, to be performed in the liquid phase.

In a third aspect, the present invention consists in a method of detecting an environmental signal comprising exposing a biosensor according to the second aspect of the present invention to the signal such that the signal induces the expression of the reporter molecule of the cells in the biosensor, prior to or during exposure the cells being induced to produce the enzyme such that substrate is formed in the cells, allowing the reporter molecule to react with the pre-formed substrate to form a detectable reaction, and detecting the reaction.

In order that the present invention may be more clearly understood, preferred forms will be described with reference to the following drawings.

BRIEF DESCRIPTION OF THE DRAWINGS

FIG. 7 is a diagram of the features of construct designated pXylR;

FIG. 8 is a diagram of the construct designated pTU/M;

DETAILED DESCRIPTION OF THE INVENTION

Figure 1:
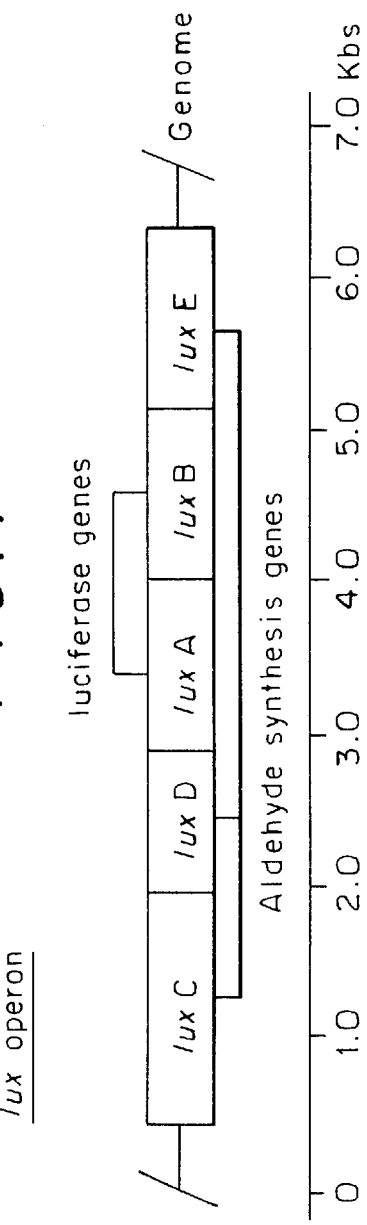
FIG. 1 is a diagram of the lux operon.

All components used in this invention are readily available to the public (except for the different constructs generated specifically for this work).

MATERIALS & METHODS

Culture Conditions

Recombinant strains of Escherichia coli were routinely cultured aerobically at 37° C. in Luria broth (LB)—tryptone 10 g/L, NaCl 10 g/L and yeast extract 5 g/L. Media was solidified by the addition of 15 g/L Kobe agar. Filter sterilised antibiotics were added as required. Ampicillin at 100 mg/ml was used to maintain constructs based on the following vectors: pSP72, pUC18, pTrc 99A and pPL-L; and tetracycline at 10 mg/ml for constructs based on pRK404. The different carbon sources used were glucose (1% w/v) and lactose (1% w/v).

General Recombinant DNA Procedures

Restriction enzymes and other DNA modifying enzymes were used under the conditions specified by the suppliers. Standard procedures as described by Sambrook et al (1989) were used for manipulating and cloning DNA. Isolation of plasmid DNA from *E. coli* was performed according to the method described by Morelle (1989), for rapid screening of plasmid-bearing clones.

TABLE 1

Description of clones constructed during this study

| Constructs | Vector | Comments/description |
| --- | --- | --- |
| pxylac-R | pRK404 | XylR ORF fused to lacZ promoter |
| pXylR | pRK404 pRK404 | XylR gene including $P_r$ cloned into the PstI/BamHI site of |
| pTer | pSP72 | Contains both rrnbT1T2 April 96 terminators |
| pTu | pSP72 | Pu cloned into the EcoRI/SmaI site of pTer |
| pluxAB | pUC18 | luxAB genes fused to lacZ promoter |
| pTLU | pSP72 | luxAB genes fused to Pu promoter in pTu |
| pluxCDE | pTrc 99A | luxCDE genes fused to trc promoter |
| pluxCDABE | pTrc 99 | luxCDABE genes fused to trc promoter |

TABLE 1-continued

Description of clones constructed during this study

| Constructs | Vector | Comments/description |
|---|---|---|
| pTluxCDABE | pSP72 | luxCDABE genes cloned into pTer |
| pLu-x | pSP72 | luxCDABE genes fused to Pu promoter in pTu |
| pLEU | pTrc 99A | Pu-luxAB detection cassette cloned into the BamHI/PstI site of pluxCDE |

TABLE 2

Description of clones constructed during this study

| Constructs | Vectors | Date constructed |
|---|---|---|
| pxylac-R | pRK404 | available in Aug 1994 |
| pXylR | pRK404 | constructed 21.4.96 (page 6, Karen Jury's labbook) confirmed 26.4.96 (page 8, Karen Jury's labbook) |
| pTer | pSP72 | available in Aug 1994 |
| pTu | pSP72 | available in Aug 1994 |
| pluxAB | pUC18 | constructed 3/7/95 (page 28121, Tony Vancov labbook 1) confirmed 6/7/95 (page 28125, Tony Vancov labbook 1) |
| pTLU | pSP72 | constructed 25/7/95 (page 28141, Tony Vancov labbook 1) confirmed 1/8/95 (page 28146, Tony Vancov labbook 1) |
| pluxCDE | pTrc 99A | constructed 25/7/95 (page 28141, Tony Vancov labbook 1) confirmed 9/8/95 (page 28153, Tony Vancov labbook 1) confirmed aldehyde producer 10/8/95 (page 28154, Tony Vancov labbook 1) |
| pluxCDABE | pTrc 99 | constructed 13/11/95 (page 9122, Tony Vancov labbook 2) confirmed 17/11/95 (page 9124, Tony Vancov labbook 2) |
| pTluxCDABE | pSP72 | constructed 16/5/96 (page 33417, Tony Vancov labbook 3) confirmed 17/5/96 (page 15, Karen Jury's labbook) |
| pLu-x | pSP72 | constructed 21/4/96 confirmed 21/4/96 luciferase assay (page 5, Karen Jury's labbook) confirmed 21/4/96 (gel digest, page 6 Karen Jury's labbook) |
| pLEU | pTrc 99A | constructed 8/12/95 (page 9142, Tony Vancov labbook 2) confirmed 13/12/95 (page 9143, Tony Vancov labbook 2) confirmed 14/12/95 (plate assay, page 9144, Tony Vancov labbook 2) |

TABLE 3

Recombinant E. coli strains

| Code | E. coli strain | Constructs* | Date obtained |
|---|---|---|---|
| Tlu-lacR | NM522 | pTLU + pxylac-R | constructed 7/8/95 (page 29151, Tony Vancov labbook 1) confirmed 10/8/95 (page 28154, Tony Vancov labbook 2) |
| Leu-lacR | NM522 | pLEU + pxylac-R | constructed 16/4/96 (page 33404, Tony Vancov labbook 3) confirmed 20/4/96 (pages 33407 and 33408 Tony Vancov labbook 3) |
| Leu-R | NM522 | pLEU + pXylR | constructed 10/5/96 (clone (i)e in Karen Jury's labbook) confirmed 11/5/96 (luminometer readings and gels, page 13 Karen Jury's labbook) |
| Lux-LacR | NM522 | pLu-x + pxylac-R | constructed 17/5/96 (page 33418, Tony Vancov labbook 3) confirmed 18/5//86 (pages 14–16, Karen Jury's labbook) |
| Lux-R | NM522 | pLu-x + pXylR | constructed 10/5/96 (clone (ii)g in Karen Jury's labbook) confirmed 11/5/96 (luminometer readings and gels, page 13 Karen Jury's labbook) |

*note that constructs carrying the XylR regulatory gene (pXylR or pxylac-R) are located on the pRK 404 plasmid whilst the actual light generating elements of the sensor are inserted in the plasmids pSP72 (pLu-x) or pTrc 99A (pLEU).

Bioluminescence Assays—Preparation of Culture

Unless otherwise stated, E. coli clones were inoculated from a fresh agar plate into a flask containing 40 ml of LB media with the appropriate antibiotics and grown aerobically (with shaking) at 37° C. for approximately 2–3 hr. The culture was harvested at an $OD_{600}$ of approximately 0.8–1.2, washed twice and resuspended in a buffer containing: 100 mM Phosphate buffer pH 7.5, ¹⁄₁₀th diluted LB broth and 0.1% glucose (w/v). In some cases, specified in the text, inducers and/or effectors such as IPTG and m-xylene (1 mM) were added. The optical density of the culture was adjusted to 1.6 and assayed as follows:

Ten ml of cell suspension were poured into in a 100 ml tightly sealed bottle (Schott bottle) which was placed on a magnetic stirrer at room temperature for the duration of the experiment. Sampling was performed at either 20 min or 30 min intervals. An aliquot of 100 ml of culture was removed and the optical density of the culture was measured at 600 nm to measure biomass content. The light production (bioluminescence in Lumi Counts Per Second, LCPS) was measured with a MicroBeta scintillation counter using microtiter plates. Twenty µl of 20% glucose were added to each well of the micro-titre plate (glucose acts as an electron donor). In each sample, luminescence activity was recorded with and without the addition of 0.5% tetradecyl aldehyde. Specific activity is determined by dividing the LCPS by the $OD_{600}$.

Aldehyde Indicator Plates

Mixtures of pararosaniline and bisulfite are often referred to as Schiffreagent and have been widely used to detect aldehydes (Lillie 1977). These components have been incorporated into a solid medium which can be used to identify clones expressing enzymes that produce aldehydes. Indicator plates were prepared by adding 8 ml of pararosaniline (2.5 mg/ml of 95% ethanol) and 100 mg of sodium bisulfite to precooled Luria agar. The plates were stored at room temperature, away from fumes containing aldehydes and light, both of which promote increased background colour.

RESULTS

Cloning of Luciferase Components a) Background

The luxAB gene products from *X. luminescens* are thermally more stable (up to 45° C.) than those of other bacteria (only up to 30° C.—Szittner and Meighen, 1990). The lux genes of this species were therefore used in the construction of this invention. The order of the lux structural genes in this organism is luxCDABE, with the luciferase genes flanked by the luxCD and luxE genes (see FIG. 1).

b) Cloning of Lux AB Genes

In the absence of a commercially available promoter detecting lux system, work was undertaken to develop such a system. The promoterless luxAB gene cassette is designed to contain unique cloning sites (EcoRV, ClaI and EcoRI) situated immediately upstream from the ribosomal binding site (RBS) of the luxA gene, flanking transcriptional terminators ($rrnbT_1T_2$), and at minimum two unique enzyme sites (BamHI and XhoI or Sal I or Pst I) which would facilitate its cloning into other vectors. Promoter sequences inserted at the EcoRV, ClaI and EcoRI sites and in the correct orientation, have the potential to express the luxAB genes.

The purpose of the $rrnbT_1T_2$ terminators upstream of the EcoRV site is to prohibit transcription from other promoters into continuing into the lux genes, while those distal to the lux genes assist in preventing the destabilisation of the host-vector system.

To facilitate the cloning of the $rrnbT_1T_2$ terminators in the different positions on pSP72, two sets of PCR primers were designed. Initially the rear terminator was amplified from the vector pKK232-8 (Brosius, 1984) and cloned into the BamHI/XbaI site of pSP72, resulting in pT2. BglII and BamHI produce compatible cohesive ends, however the religated ends cannot be recleaved by either enzyme. Hence, the original BamHI and BglII restriction sites in pSP72 and the $rrnbT_1T_2$ PCR product respectively do not exist in pT2. The forward transcriptional terminator was similarly amplified and cloned into the BglII/EcoRV site of pT2. A positive clone (designated PTER) was isolated, characterised and retained for further study.

Figure 2:
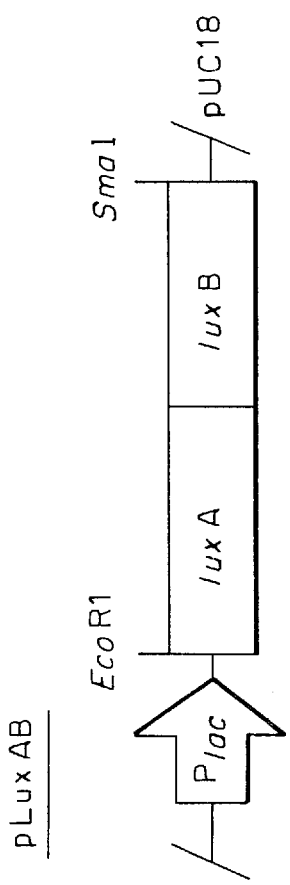
FIG. 2 is a diagram of clone designated pLuxAB.

The luxAB genes from *X. luminescens* were amplified and cloned into the EcoRI/SmaI site pUC18, resulting in a transcriptional fusion between the vector's lacZ promoter and the luxAB genes. Bioluminescence of colonies carrying this construct were easily visualised in the dark with the naked eye, on addition of exogenous aldehyde. Characterisation of constructs isolated from ten randomly picked colonies were found to be identical to each other and genuine. One clone, designated pluxAB, was retained (see FIG. 2).

c) Cloning the Aldehyde Synthase Genes

Figure 3:
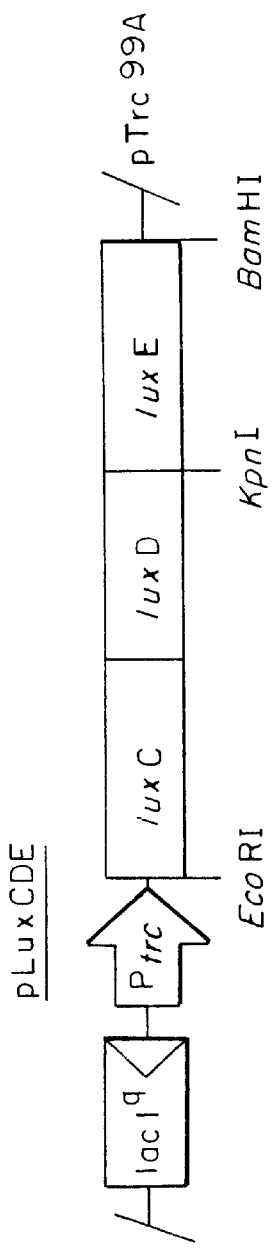
FIG. 3 is a diagram of clone designated pLuxCDE.

The luxCDE genes were placed under the transcriptional control of the trc promoter which contains the trp (−35) region and the lac UV5(−10) region separated by 17 base pairs (Amann et al., 1988). The PCR fragment generated by the luxCD primers was restricted with Eco RI/Kpn I and ligated to the Kpn I/Bam HI restricted luxE PCR product. Unique restriction enzyme sites were incorporated and positioned at the 5' termini of each primer. The nucleotide sequence of the primers and the conditions of amplification are listed in the appendix. The resulting ligation mixture was subjected to an additional 25 rounds of amplification with the luxCD forward and luxE reverse primers. The final product comprising luxCDE (approx. 3.7 Kb) was cloned into the EcoRI/BamHI sites of the expression vector pTrc 99A and transformed into NM522. Positive aldehyde producing clones were isolated by patching transformants onto aldehyde indicator plates. Subsequent PCR and RE analysis of randomly picked clones, verified the authenticity of the constructs. A clone designated pLuxCDE (see FIG. 3), was retained for additional work.

The plasmid pTrc 99A contains the strong trc promoter which is inducible by IPTG. Furthermore, the vector contains the lacZ ribosomal binding site and the lacIq repressor, which controls the promoter. The trc promoter, however, is a very strong promoter and has been shown to initiate transcription at a low level even in an uninduced state (Amann et al., 1988).

d) Control Construct—Luciferase Operon

Constructs encoding the entire lux operon as a single unit, were to serve as a control. The entire lux operon (CDABE genes) was amplified from *X. luminescens* with the luxCD forward and luxE reverse primers, using Boerhinger's expand™ Long Template PCR kit. Following EcoRI and BamHI restriction, the PCR fragment was cloned into the EcoRI/BamHI site of pTrc 99A, resulting in a transcriptional fusion between the trc promoter and the lux operon. Visual examination of the resulting recombinant clones failed to yield bioluminescence in the absence or presence of exogenous aldehyde. However, luminescence was detected with the aid of the scintillation counter in the absence of exogenous aldehyde. Characterisation of these transformants via RE and PCR analysis, confirmed that the entire lux operon had been cloned. A representative of the transformants, designated pluxCDABE, was retained for additional work.

Figure 4:
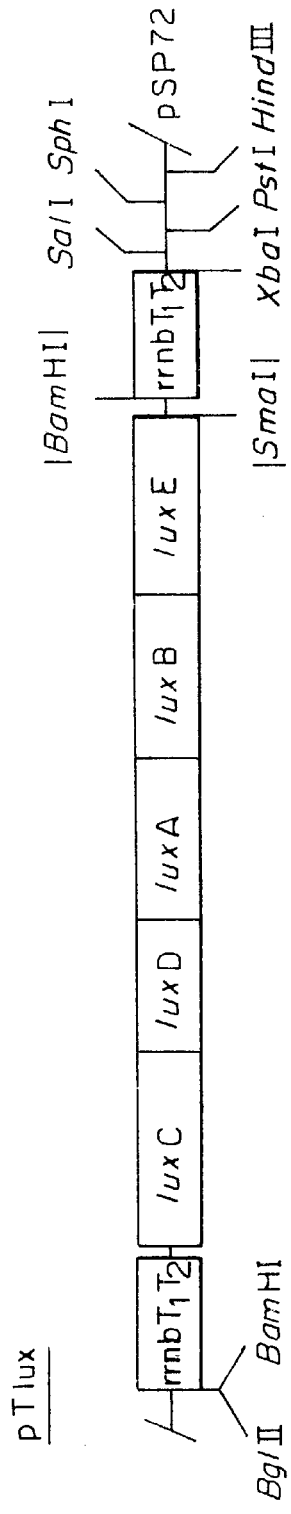
FIG. 4 is a diagram of clone designated pTlux.

To rule out the possibility of an internal promoter activating transcription of the lux operon, the PCR fragment was cloned into the EcoRI/SmaI sites of pTER. Examination with the naked eye and the scintillation counter, of the resulting recombinant clones (designated pTlux), failed to yield bioluminescence in the absence or presence of exogenous aldehyde. pTlux contains the luxCDABE genes flanked two transcriptional terminators (outlined in the FIG. 4).

Construction of BTEX Sensor a) Background

Figure 5:
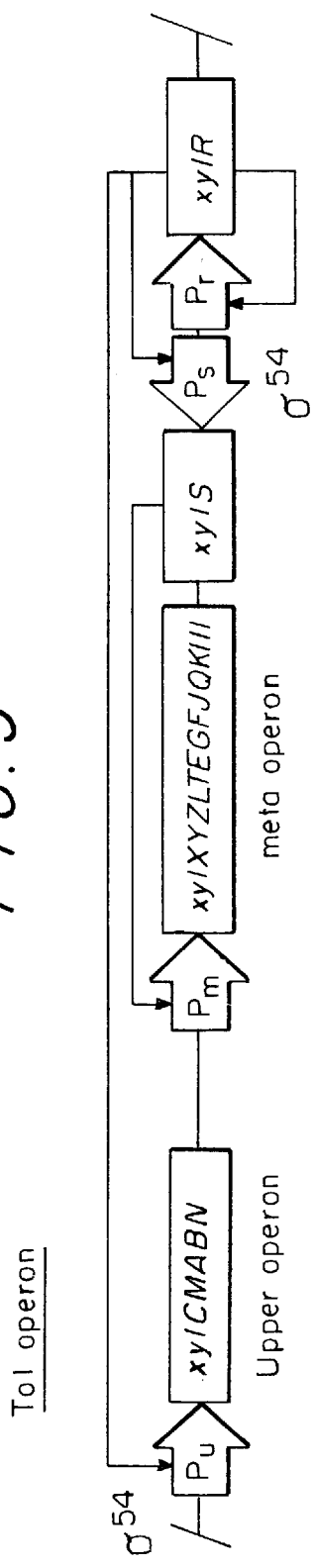
FIG. 5 is a diagram of the two operons controlling the genes encoding the degradation of toluene, the Tol operon.

The Tol plasmid of Pseudomonas putida encodes for enzymes required in the complete degradation of toluene, m-xylene and p-xylene (Wang & Dunn, 1974; Worsey & Williams, 1975). The genes encoding the degradation of toluene are organised in two operons (see FIG. 5). The 'upper' pathway is responsible for the oxidation of toluene and xylenes to aromatic carboxylic acids (Franklin et al, 1983). In addition to the genes for catabolic enzymes, the Tol plasmid encodes for the XylR regulatory protein which in concert with upper pathway effectors (such as toluene) triggers expression from the pathway operon promoter (Pu, Abril et al., 1989).

b) Cloning the Regulatory Genes

Figure 6:
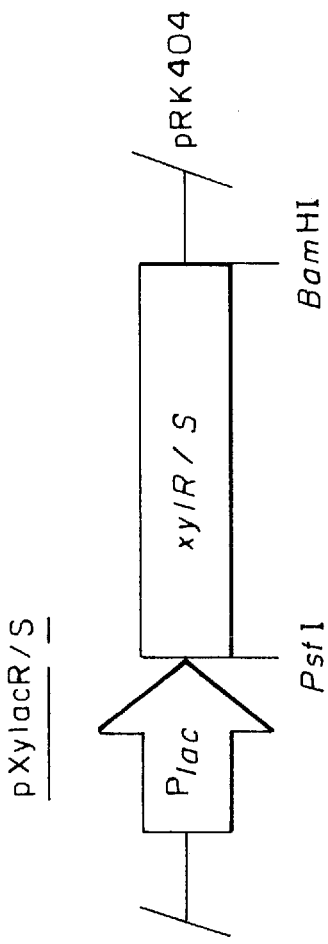
FIG. 6 is a diagram of pXlacR/S.

The xylR gene was amplified (via PCR) from the archetypal Tol plasmid, and individually cloned into the PstI/BamHI site of the broad host range vector pRK404 (Ditta et al, 1985). The resulting constructs are under the transcriptional control of the inducible lacZ promoter, as shown in FIG. 6.

Since the xylR gene contains an internal PstI site, an NsiI restriction site was introduced at the 5' end of the xylR gene product via the forward PCR primer. This primer contains a recognition site for NsiI. Cleavage with NsiI produces compatible cohesive ends with PstI, thus facilitating ligation. The resulting construct, designated pxylac-R, contains the open reading frame (ORF) of the xylR gene.

The entire xylR gene (including its promoter—$P_r$) was also cloned. The rationale for creating this construct was to demonstrate that strains containing heterologous genes would respond to BTX compounds more rapidly than strains harbouring archetype genes. The entire xylR gene (2.1 kb) was amplified (via PCR) from the Tol plasmid, and cloned into the PstI/BamHI site of pRK404. To rule out transcriptional interference from the lacZ promoter, the xylR gene was cloned in the opposite orientation. This was assisted by exchanging the restriction sites of the forward and reverse PCR primers. Thus, the forward primer contains a BamHI recognition site at the 5' end and similarly the reverse primer contains an NsiI site. A diagram illustrating the features of the resulting construct pXylR, is depicted in FIG. 7.

c) Fusing the Catabolic Promoters to the Lux Detection System

The next step of this objective was to clone the promoter of the upper pathway of the Tol plasmid into pTER. The promoter was amplified from the Tol plasmid, individually ligated into the EcoRV/EcoRI sites of PTER and transformed into *E. coli* HB101. Following PCR and restriction endonuclease analysis, two clones were isolated and retained for future work. The construct harbouring the Pu promoter is designated pTU (refer to FIG. 8).

Having established that the luxAB genes from *X. luminescens* were functionally transcribed in *E. coli*, the genes were subsequently cloned into pTU. The luxAB PCR fragment was restricted with Eco RI following blunting, and individually ligated into the Eco RV/ Eco RI site of pTU, generating pTLU. Visual examination of the resulting recombinant clones failed to yield bioluminescence in the presence of exogenous aldehyde.

Luminescence, however, was detected with the aid of the scintillation counter. A loop full of cells were scraped of the agar plate and resuspended in an eppendorf tube containing 100 ml of Luria broth plus 1% tetradecyl aldehyde. The culture was transferred to polystyrene micro-titre plates and scanned for light production using the scintillation counter. Characterisation of these transformants via RE and PCR analysis, verified that the constructs were authentic.

Figure 9:
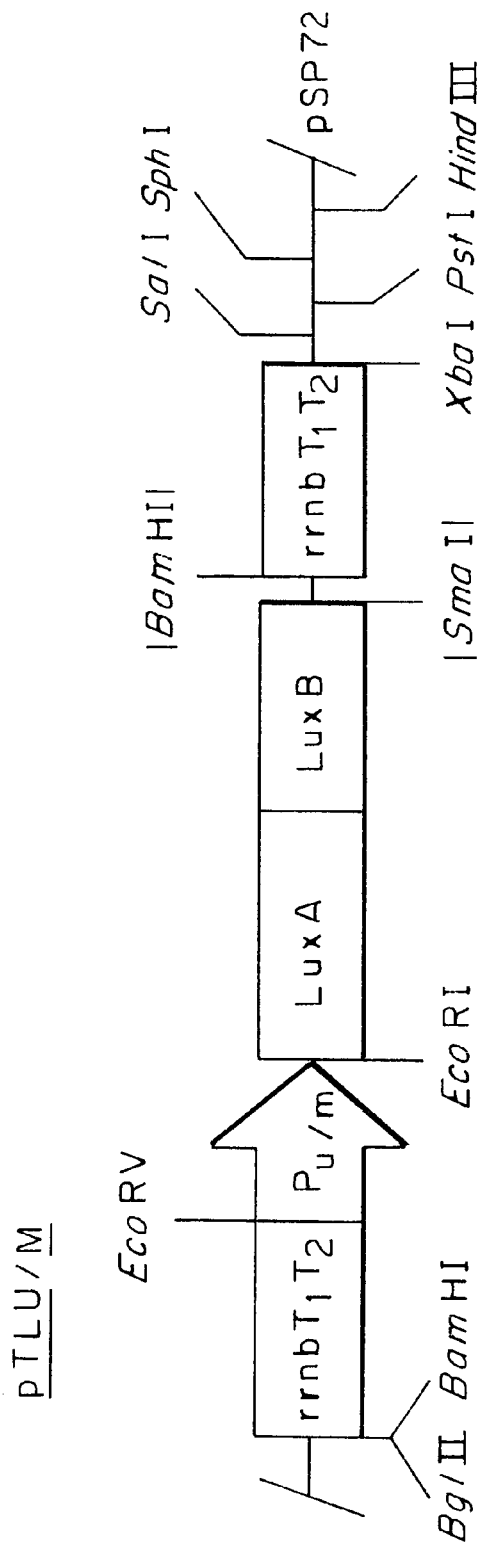
FIG. 9 is a diagram showing the respective positions of the components in pTLU/M.

A diagram illustrating the respective position of the construct's components is shown in FIG. 9.

d) Transcription of Pu Promoter Constructs

To confirm the potential usefulness of pTLU, luciferase activity of these clones was examined in response to the known effector m-xylene. *E coli* strains containing the clone and its specific regulator (pxylacR) were also examined (see Table 4). In *E coli* NM522 containing pTLU a relatively low level of luminescence was detected. These results are in agreement with previous findings (Hugouvieux-Cotte-Pattatet al., 1990), which have shown that Pu can initiate transcription in the absence of its regulator.

Expectedly, XylR-dependent expression of the Pu promoter increased from 40 to 470 fold, depending on the type of sugar and/or IPTG present. A 5 to 10 fold decrease in light output was observed in the absence of the effector molecule (m-xylene), for all organisms except for those grown with glucose. The highest xylene-induced luciferase activity was recorded with cells grown in the presence of glucose (7.5× $10^5$ LCPS). Some caution must be exercised in interpreting these results, since glucose is known to repress transcription from the lacZ promoter (XylR is transcribed from the lacZ promoter).

TABLE 4

Luminescence activities of recombinant *E. coli* (NM522) strains containing the TOL xylR regulators and the 'upper' promoter luxAB construct.

| Constructs | Supplements | LCPM |
|---|---|---|
| pLuxAB | +IPTG | $6.2 \times 10^6$ |
| pLuxAB | −IPTG | $8.9 \times 10^5$ |
| pxylacR | +IPTG, +xylene | —$^a$ |
| pxylacR | +IPTG, −xylene | —$^a$ |
| pTLU | +IPTG, +xylene | $1.6 \times 10^3$ |
| pTLU | +IPTG, −xylene | $2.3 \times 10^3$ |
| pxylacR-pTLU | +xylene | $6.6 \times 10^4$ |
| pxylacR-pTLU | −xylene | $1.8 \times 10^4$ |
| pxylacR-pTLU | +IPTG, +xylene | $4.3 \times 10^5$ |
| pxylacR-pTLU | +IPTG, −xylene | $8.6 \times 10^4$ |
| pxylacR-pTLU | +glucose, +xylene | $7.5 \times 10^5$ |
| pxylacR-pTLU | +glucose, −xylene | $4.2 \times 10^5$ |
| pxylacR-pTLU | +lactose, +xylene | $3.4 \times 10^5$ |
| pxylacR-pTLU | +lactose, −xylene | $4.8 \times 10^4$ |

Figure 10:
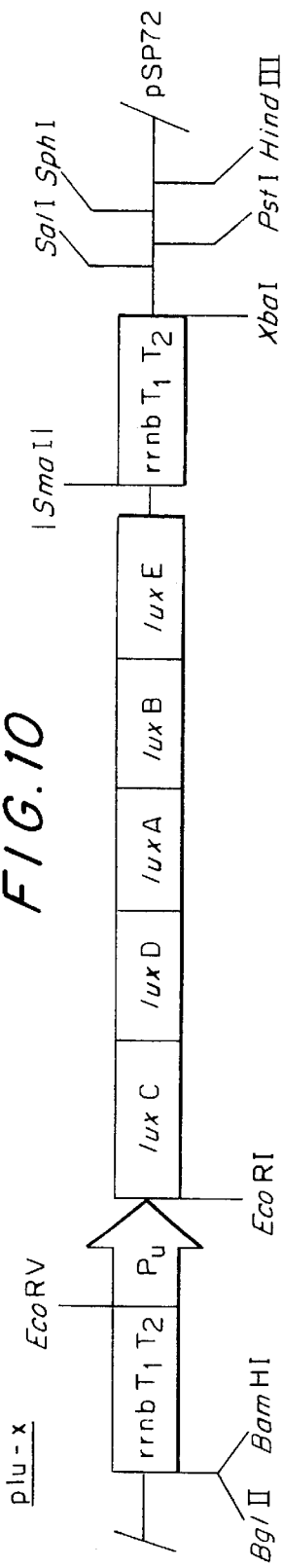
FIG. 10 is a diagram of a representative of the transformant designated plu-x.

Overnight cultures of the recombinant strains were diluted 100-fold into LB broth containing ampicillin and tetracycline at a concentration of 100 and 10 mg/ml, respectively. The carbon source, glucose and lactose was provided at a concentration of 1%. To induce expression of the regulatory gene XylR, IPTG was added at a concentration of 1 mM. Luminescence activities (Luminescence Counts Per Second) were determined after 5 hr in the presence of the effector m-xylene (1 mM) and the addition of 2 ml of 10% tetradecylaldehyde. Cultures were grown at 30° C.
-$^a$, Not detected e) BTEX Sensor Control Constructs The lux operon (control construct) was placed under the control of the Pu promoter. As previously mentioned, the entire lux operon (CDABE genes) was amplified from *X. luminescens* using Boerhinger 's expand™ Long Template PCR kit. The PCR fragment, restricted with EcoRI at the 5' end and blunt at the 3' end, was ligated into the EcoRI/SmaI sites of pTu. Following transformation into NM522, positive bioluminating clones were identified in the absence of exogenous aldehyde with the scintillation counter. Restriction endonulease and PCR analysis was used to determine their authenticity. A representative of the transformants, designated pLu-x, was retained for additional work (see FIG. 10). An attempt was made to determine the background luminescence activity. pLu-x was cultured in Luria broth and assayed according to the protocol described in the method and materials section. No luminescence was detected in the presence or absence of exogenous m-xylene.

f) Construction of Complete BTEX Sensor

Figure 11:
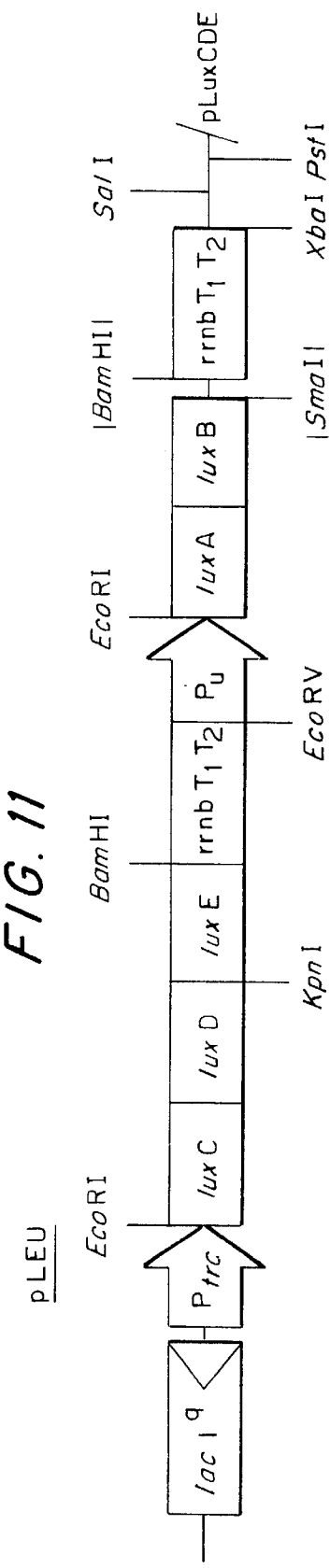
FIG. 11 is a diagram of a representative of the transformant designated pLEU.

The Pu-luxAB cassette was isolated from pTLU via agarose gel electrophoresis following restriction with BamHI/PstI, and cloned into the similarly restricted sites of pluxCDE. Characterisation of these transformants via RE and PCR analysis, confirmed that the Pu-luxAB cassette was fused to the luxCDE genes. A representative of the transformants, designated pLEU, was retained for additional work. The relative position of the Pu-luxAB cassette in pLEO is outlined in FIG. 11. In order to determine the background luminescence activity, pLEU was cultured in Luria broth and assayed according to the protocol described in the materials and methods section. Repeated assays failed to show luminescence, even in the presence of m-xylene. These results clearly indicate lack of induction of Pu in the absence of the regulatory protein Xyl R.

The test strain Leu-lacR was created by transforming both pLEU and pxylac-R into NM522 and selecting for resistance to ampicillin and tetracycline. Similarly, Leu-R, Lux-lacR and Lux-R were produced by transforming the respective constructs (refer to Tables 1 and 2) into NM522.

Figure 12:
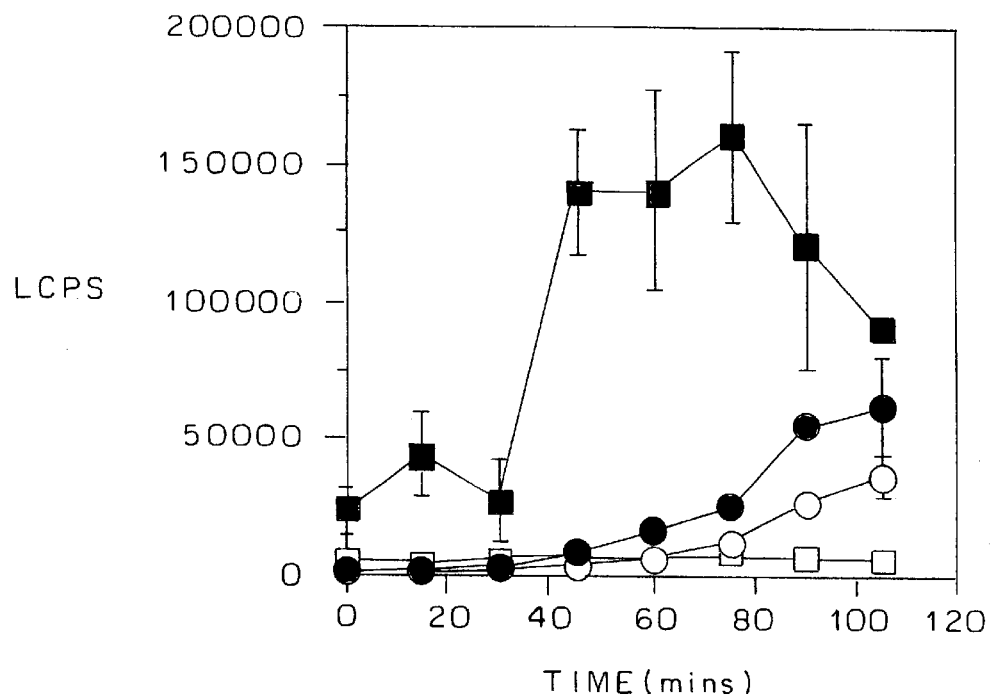
FIG. 12 shows the time course of bioluminescence of the new sensor construct (Leu-lacR) with addition of xylene (full squares) and without addition of xylene (open squares) as well as the corresponding data for the control construct (Lux-lacR) where closed and open circles represent the response in the presence of xylene and in the absence of xylene, respectively.
Figure 13:
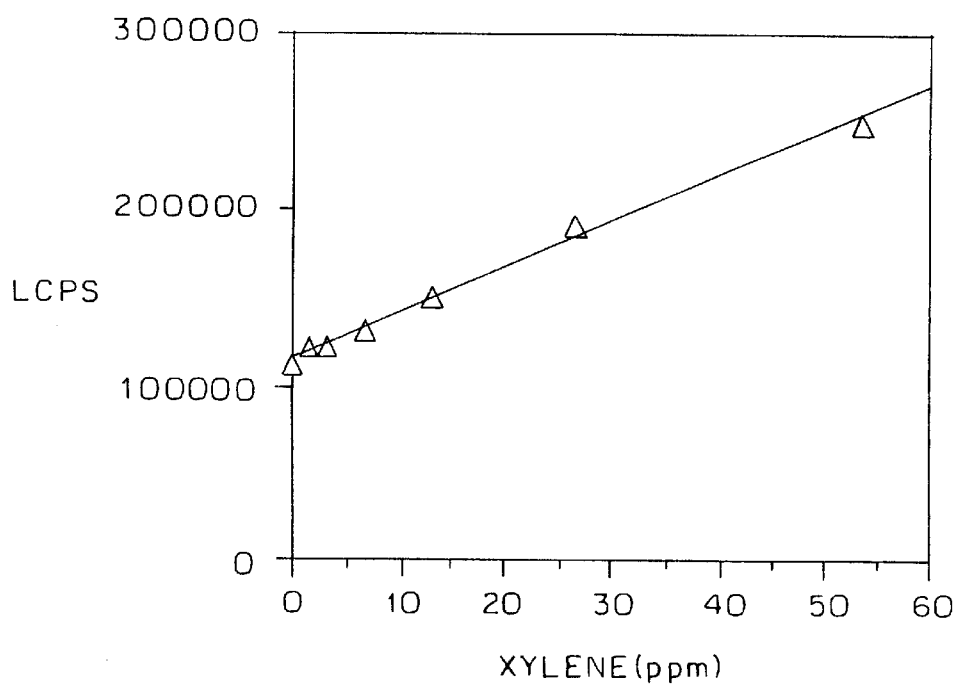
FIG. 13 shows a calibration curve obtained with the new sensor construct (Leu-lacR). The organisms were inoculated from a glycerol stock and grown overnight at 30° C. with minimal agitation.
Figure 14:
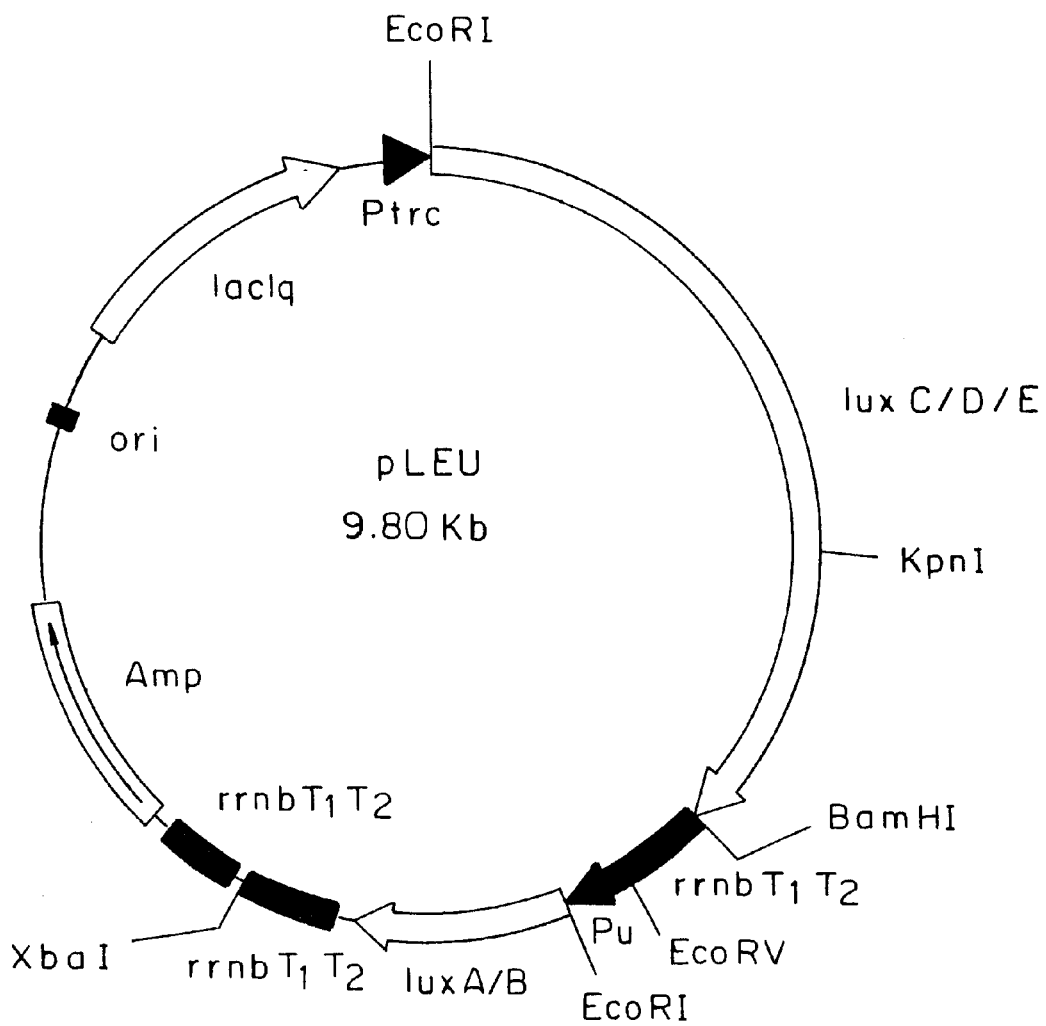
FIG. 14 shows a map pf plasmid pLEU.

Assay results of these strains are presented in FIG. 12. and FIG. 13.

The functionality of the novel sensor of the present invention is demonstrated in FIGS. 12 and 13. The response of the new sensor was clearly superior to that obtained with

```
    5'                          3'
    CCAATGCATTGTGGATCATCCCGATAAAAA    (SEQ ID NO:1)
      Nsi I
    Tm - 52.0° C.          G.C. - 40%
``` the reference construct based on the native lux gene cassette. The induction of the light signal was faster and much more intensive in the new sensor. FIG. 13 clearly shows that linear calibration curves can be obtained with such sensors down to sub-ppm levels in the case of xylene. Sensor responses are therefore significantly improved by splitting of lux genes as achieved in the novel sensor constructs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

Abril, M. A., Michan, C., Timmis, K. N., and Ramos, J. L.(1989) *J. Bacteriol.* 171:6782–6790.

Amann, E.; Ochs, B. & Abel, K.-J.(1988) *Gene* 69:301–315.

Brosius, J. (1984) *Gene*, 27:151–160.

Burlage, R. S. & Kuo, C.-T. (1994) *Annu. Rev. Microbiol.* 48, 291–309.

Ditta, G., Schmidhauser, T., Yakobson, E., Lu, P., Liang, X. W., Finlay, D. R., Guiney, D. and Helinski, D. R. (1985) *Plasmid* 13: 149–153.

Franklin, F. D. C., Lehrbach, P. R., Lurz, R., Rureckert, B., Bagdasarian, M. and Timmis, K. N.(1983) *J. Bacteriol.* 154: 676–685.

Hugouvieux-Cotte-Pattat, N.,Kohler, T., Rekik,. M., and Harayama, S. (1990) *J. Bacteriol.* 172:6651–6660.

King, J. M. H., DiGrazia, P. M., Applegate, B., Burlage, R., Sanseverino, J., Dunbar, P., Larimer, F. and Sayler, G. S. (1990) *Science* 249:778–781.

Lillie, R. D. (1977) *Conn's biological stains*, 9th ed., p. 259–266. The Williams & Wilkins Co. Baltimore.

Meighen E. A. *Ann. Rev. Genetics*, 28, 117–139, (1994).

Morelle, G. (1989) A plasmid extraction procedure on a miniprep scale. *Focus (BRL, USA)* 11.1:7–8.

Sambrook, J., Fritsch, E. F. and Maniatis, T. (1989) *Molecular Cloning*: A laboratory manual, Cold Spring Harbor Laboratory, Cold Spring Harbor, N.Y.

Szittner, R. and Meighen, E. (1990) *J. Biol. Chem.* 265:16581–16587

Worsey, M. J. and Williams, P. A. (1975) *J. Bacteriol.* 124: 7–13. Baldwin, T. O.; Berends, T.; Bunch, T. A.; Holzman, T. F.; Rausch, S. K.; Shamansky, L.; Treat, M. L. and Ziegler, M. M. (1984) *Biochemistry* 23, 3663–3667.

Wang, C. L. & Dunn, N. W. (1974) *Genetical Research* 23, 227–232.

Appendix 1

PCR of the XylR gene from the TOL plasmid in *Pseudomonas putida*.

According to computer analysis (PCR primer and Amplify) the following primers were used:

XylR geneXylR ORF:

Forward primer ($R_F$): 30 mer

```
    5'                               3'
    CCAATGCATTGTGGATCATCCCGATAAAAA    (SEQ ID NO:1)
      Nsi I
    Tm - 52.0° C.          G.C. - 40%
```

Reverse primer ($R_R$): 28 mer

```
    5'                           3'
    CGGGATCCCGCCCGTTTTCACACAACCT      (SEQ ID NO:2)
      Bam HJ
    Tm - 60.9° C.          G.C. - 60%
```

PCR conditions: primers annealed for 30 secs. at 46° C., extention time of 2.5 mins. for 30 cycles.

Resulting product size: Approx. 1963 bps

XylR entire gene:

Forward primer (XylRN.for): 29 mer

```
    5'                            3'
    CGGGATCCCGGATCTGCGTTGAGGTGGAT     (SEQ ID NO:3)
      BamHI
    Tm - 62.4° C.          G.C. - 62%
```

Reverse primer (XylRn.rev): 29 mer

```
    5'                            3'
    CCAATGCATTGCCCGTTTTCACACAACCT     (SEQ ID NO:4)
      NsiI
    Tm - 60.9° C.          G.C. - 48%
```

PCR conditions: primers annealed for 30 secs. at 45° C., extention time of 2.5 mins. for 30 cycles.

Resulting product size: Approx. 2111 bps

Terminators

PCR the *Escherichia coli* 5s ribosomal RNA terminators ($rrnbT_1T_2$) from the vector pkk232-8. According to computer analysis (PCRprimer and Amplify) the following primers were designed:

Forward Terminator

Forward primer (Frnb.F): 36 mer

```
    5'                                      3'
    GAAGATCTTCGGGATCCTCAGAAGTGAAACGCCGTA    (SEQ ID NO:5)
      Bgl II  Bam HI
    Tm - 59.1° C.             G.C - 50%
```

Reverse primer (Frnb.R): 27 mer

```
    5'                          3'
    CGGATATCCTGATGCAAAAACGAGGCT     (SEQ ID NO:6)
      Eco RV
    Tm - 62° C.    G.C - 50%
```

Product size: Approx. 390 bps

Rear Terminator
Forward primer (Rrnb.F): 26 mer

```
5'                              3'
GAAGATCTCAGAAGTGAAACGCCGTA        (SEQ ID NO:7)
  Bgl II
Tm - 59.1° C.        G.C - 50%
```

Reverse primer (Rrnb.R): 29 mer

```
5'                                    3'
GCTCTAGAGCCTGATGCAAAAACGAGGTC (SEQ ID NO:8)
   Xba I
Tm - 62° C.                G.C -
50%
```

Product size: Approx. 380 bps
PCR conditions for both products: primers annealed for 10 secs. at 63° C., extention time of 30 secs. for 20 cycles.

Xenorhabdus Luminescens Lux CDABE Genes

PCR the lux operon (CDABE) genes (including the ribosomal binding site) from *X. luminescens*. The following gene(s) were amplified as a single unit:

lux CD
lux AB
lux E
entire operon lux CDABE

According to computer analysis (PCR primer and Amplify) the following primers were used:

Lux CD:
Forward primer (luxCD.F): 26 mer

```
5'                          3'
GGAATTCCCCCCGATTAAATGGATGGC        (SEQ ID NO:9)
  Eco RI
Tm - 62.2° C.        G.C. - 53%
```

Reverse primer (luxCD.R): 32mer

```
5'                                3'
GGGGTACCCCGCAAAAAGTTTCCAAATTTCAT   (SEQ ID NO:10)
  KpnI
Tm - 57.4° C.        G.C. - 27%
```

PCR conditions: primers annealed for 30 secs. at 52° C., extention time of 2.5 mins. for 25 cycles.
Resulting product size: Approx. 2483 bps

Lux: AB
Forward primer (lux.F): 32 mer

```
5'                                  3'
CGGAATTCCGAAGGACTCTCTATGAAATTTGG   (SEQ ID NO:11)
  Eco RJ
Tm - 54.4° C.        G.C. - 36%
```

Reverse primer (lux.R): 18 mer

```
5'                  3'
CCTCCCTGCAACTCGAAAT                (SEQ ID NQ:12)
Tm - 61.5° C.        G.C. - 53%
```

PCR conditions: primers annealed for 30 secs. at 50° C., extention time of 2.0 mins. for 25 cycles.
Resulting product size: Approx. 2114 bps

Lux E:
Forward primer (luxE.F): 32 mer

```
5'                                 3'
GGGGTACCCCCTTGAGGAGTAAAACAGGTATG  (SEQ ID NO:13)
  KpnI
Tm -53.4° C.        G.C. - 41%
```

Reverse primer (luxE.R): 30 mer

```
5'                              3'
GCAAGGGATCCACTTACAATTAGGCAAAGG    (SEQ ID NO:14)
  Bam HI
Tm - 58.3° C.        G.C. - 41%
```

PCR conditions: primers annealed for 30 secs. at 45° C., extention time of 2.0 mins. for 25 cycles.
Resulting product size: Approx. 1205 bps

Lux operon
Forward primer (luxCD.F): 25 mer

```
5'                       3'
GTTGGAATTCCCCCCGATTAAATGG          (SEQ ID NO:15)
    Eco RI
Tm - 62.2° C.        G.C. - 53%
```

Reverse primer (luxE.R): 30 mer

```
5'                              3'
GCAAGGGATCCACTTACAATTAGGCAAAGG    (SEQ ID NO:16)
   Bam HI
Tm - 53.3° C.        G.C. - 41%
```

PCR conditions: Used the Boerhinger expand™ Long Template PCR kit. Essentually the first 10 cycles were as follows:—denature 94° C. for 10 secs.
  anneal at 52° C. for 30 secs.
  elongation at 68° C. for 5 mins.
Then 15 cycles as follows:—denature 94° C. for 10 secs.
  anneal at 52° C. for 30 secs.
  elongation at 68° C. for 5 mins. with a 20 sec incremental increase in each elongation step.
Resulting product size: Approx. 5831 bps

Upper Toluate Catabolic Pathway Promoter Region

PCR the upper toluate catabolic pathway promoter (including the ribosomal binding site) from the TOL plasmid in *Pseudomonas putida*. According to computer analysis (PCRprimer and Amplify) the following primers are to be used:

Forward primer ($U_F$): 19 mer

```
5'                  3'             (SEQ ID NO:17)

GGAAAGCGCGATGAACCTT

Tm - 62.6° C.   G.C. - 53%
```

Reverse primer ($U_R$): 28 mer

```
5'                          3'     (SEQ ID NO:18)

GCGAATTCCTGAAGGGTCACCACTATTT

Eco RI
```

```
Tm - 61.5° C.      G.C. - 53%
```

PCR conditions: primers annealed for 10 secs. at 58° C., extention time of 30 secs. for 25 cycles.
Resulting product size: Approx. 246 bps Appendix 2

Examples of promoters which may be used as sensor elements:

| Promoter | Signal | Reference |
|---|---|---|
| mer | heavy metals (particularly mercury) | Selinofova, O.; Burlage, R. and Barkay, T., Appl. Env. Microbiol., 59, 3083–3090, 1993. |
| Psal | naphthalene, salicylate | Heitzer, A.; Webb, O. F.; Thonnard, J. E. & Sayler, G. S. Appl. Env. Microbiol., 58, 1839–1846, 1992. |
| fliC | aluminium | Guzzo, J.; Guzzo, A. & DuBow, M. S. Toxicol. Lett. 64/65, 687–693, 1992. |
| arsB | arsenic | Corbisier, P.; Ji, G.; Nuyts, G.; Mergeay, M. & Silver, S. FEMS Microbiol. Lett., 110, 231–238, 1993. |
| cadA | cadmium | Corbisier, P.; Ji, G.; Nuyts, G.; Mergeay, M. & Silver, S. FEMS Microbiol. Lett., 110, 231–238, 1993. |
| Pm and Ps | aromatic hydrocarbons | Abril, M. A., Michan, C., Timmis, K. N., and Ramos, J. L. J. Bacteriol. 171, 6782–6790, 1989. |
| tcb | chlorobenzenes | van der Meer, J. R., deVos, W. M., Harayama, S. & Zehnder, A. Microbiol. Rev., 56, 677–694, 1992. |
| clc | chlorobenzoates | van der Meer, J. R., deVos, W. M., Harayama, S. & Zehnder, A. Microbiol. Rev., 56, 677–694, 1992. |
| bph | polychlorinated biphenyls | van der Meer, J. R., deVos, W. M., Harayama, S. & Zehnder, A. Microbiol. Rev., 56, 677–694, 1992. |
| cat | catechol | van der Meer, J. R., deVos, W. M., Harayama, S. & Zehnder, A. Microbiol. Rev., 56, 677–694, 1992. |
| dmpR | phenols | Sze, C. C.; Moore, T. & Shingler, V. Appl. Env. Microbiol., 178, 3727–3735, 1996. |
| lac | lactose | Engebrecht J.; Simon, M. & Silverman, M. Science, 227, 1345–1347, 1985. |
| ara | arabinose | Engebrecht J.; Simon, M. & Silverman, M. Science, 227, 1345–1347, 1985. |
| rha | rhamnose | Ramos, J. L.; Rojo, F. & Timmis, K. N. Nucleic Acids Res. 18, 2149–2152, 1990. |
| mel | melibiose | Ramos, J. L.; Rojo, F. & Timmis, K. N. Nucleic Acids Res. 18, 2149–2152, 1990. |
| xyl | xylose | Ramos, J. L.; Rojo, F. & Timmis, K. N. Nucleic Acids Res. 18, 2149–2152, 1990. |
| sor | sorbose | Ramos, J. L.; Rojo, F. & Timmis, K. N. Nucleic Acids Res. 18, 2149–2152, 1990. |
| hut | histidine | Fisher, S. H.; Rohrer, K. & Ferson, A. E. J. Bact., 178, 3779–3784, 1996 |
| nifA | nitrogen assimilation | Shingler, V. Mol. Miocrobiol. 19, 409–416, 1996. |
| ntrC | nitrogen assimilation | Shingler, V. Mol. Miocrobiol. 19, 409–416, 1996. |
| laf | expression of lateral flagella in *E. coli*, induced in response to surfaces | Engebrecht J.; Simon, M. & Silverman, M. Science, 227, 1345–1347, 1985 |
| proU | osmolarity | Zhang, X.; Fletcher, S. A. & Csonka, L. N. J. Bact. 178, 3377–3379, 1996. |
| csiA | starvation | Kjelleberg, S.; Albertson, N. Flärdh, K.; Holmquist, L.; Jouper-Jaan, Å; Marouga, R.; Östling, J.; Svenblad, B. & Weichart, D. Antonie van Leeuwenhoek, 63, 3/4, 333–342, 1993. |
| sigB, ctc, gsiB, gspA, katE, gspB, gtaB, csbA | stress response of *Bacillus subtilis* | Hecker, M.; Schumann, W. & Völker, U. Mol. Microbiol., 19, 417–428, 1996. |
| dnaK | heat shock | Van Dyk, T. K.; Majarian, W. R.; Konstantinov, K. B.; Young, R. M.; Dhurjati, P. S. & LaRossa, R. A. Appl. Env. Microbiol., 60, 1414–1420, 1994. |

-continued

| Promoter | Signal | Reference |
|---|---|---|
| grpE | heat shock | Van Dyk, T. K.; Majarian, W. R.; Konstantinov, K. B.; Young, R. M.; Dhurjati, P. S. & LaRossa, R. A. Appl. Env. Microbiol., 60, 1414–1420, 1994. |
| algB | alginate biosynthesis | Shingler, V. Mol. Miocrobiol. 19, 409–416, 1996. |

-continued

| Promoter | Signal | Reference |
|---|---|---|
| cspA | cold shock | Nakashima, K.; Kanamaru, K.; Mizuno, T. & Horikoshi, K. J. Bact. 178, 2994–2997, 1996. |
| hrpS | virulence determinants | Shingler, V. Mol. Miocrobiol. 19, 409–416, 1996. |

What is claimed is:

1. A genetic construct for use in a biosensor for detecting the presence of an analyte, the construct comprising:

(a) a first nucleic acid molecule comprising a first nucleotide sequence encoding a reporter molecule having a detectable activity, the reporter molecule being bacterial luciferase Lux AB or a functional equivalent thereof; and (b) a second nucleic acid molecule comprising a second nucleotide sequence encoding an enzyme which produces a substrate for the reporter molecule, the enzyme being Lux CDE enzyme fatty acid reductase or a functional equivalent thereof, wherein the first sequence is under the control of a first promoter, which is inducible by the presence of analyte in a sample, and the second sequence is under the control of a second inducible promoter, which serves to charge a host cell with the enzyme encoded by the second sequence prior to induction of the reporter molecule such that the reporter molecule becomes immediately saturated with substrate upon its induced expression in the host cell in the presence of analyte.

2. The construct according to claim 1, wherein the first molecule encoding Lux AB and the second nucleic acid molecule encoding Lux CDE are obtained from any of the lux operons of bioluminescent microorganisms selected from the group of genera consisting of Vibrio, Xenorhabdus, Photorhabdus and Photobacterium.

3. The construct according to claim 2 for use in a biosensor for detecting xylene, wherein the first promoter is a Pu promoter.

4. The construct according to claim 3 such that the first promoter is inducible by exposure to an environmental signal, wherein induction is achieved directly by the signal or indirectly by activating one or more separate pathways in a cell containing the construct.

5. The construct according to claim 4, further comprising a nucleic acid molecule encoding an auxiliary element required for activation of the reporter molecule via its promoter.

6. The construct according to claim 1 for use in a biosensor for detecting xylene, wherein the first promoter is a Pu promoter.

7. The construct according to claim 6, wherein the second nucleic acid molecule comprises the second nucleotide sequence encoding Lux CDE operably linked to a trc promoter.

8. The construct according to claim 1, wherein the first promoter is inducible by exposure to an environmental signal, and wherein induction is achieved directly by the signal or indirectly by the signal or indirectly by activating one or more separate pathways in a cell containing the construct.

9. The construct according to claim 1, further comprising a nucleic acid molecule encoding an auxiliary element required for activation of the reporter molecule via its promoter.

10. A biosensor for measuring an environmental signal, comprising a cell transformed with the genetic construct of claim 1 and a means for measuring the activity of the reporter molecule in the cell when the cell has been exposed to the environmental signal.

11. The biosensor according to claim 10, wherein the cell is selected from the group consisting of bacterial, yeast, fungal, plant, and animal cells.

12. The biosensor according to claim 11, wherein the cell is a bacterial cell.

13. The biosensor according to claim 12, wherein the bacterial cell is *Escherichia coli*.

14. The biosensor according to claim 11, wherein the environmental signal is selected from the group consisting of pollutants, toxins, temperature, irradiation, biological signals, and chemical signals.

15. The biosensor according to claim 14, wherein the means for measuring the activity of the reporter molecule in the cell is an instrument capable of measuring light output of the cells.

16. The biosensor according to claim 15, wherein the instrument capable of measuring the light output of the cells is selected from the group consisting of photomultipliers, charge coupled devices, luminometers, photometers, fiber-optic cables, and liquid scintillation counters.

17. A method of detecting an environmental signal, comprising:
(a) exposing a biosensor according to claim 16 to the signal such that the signal induces the expression of the reporter molecule of the cells in the biosensor, wherein prior to or during exposure, the cells are induced to produce an enzyme such that substrate is formed in the cells;
(b) allowing the reporter molecule to react with the pre-formed substrate to form a detectable reaction; and
(c) detecting the reaction.

18. A method of detecting an environmental signal, comprising:
(a) exposing a biosensor according to claim 1 to a signal such that the signal induces the expression of the reporter molecule of the cells in the biosensor, wherein prior to or during exposure the cells are induced to produce an enzyme such that substrate is formed in the cells;
(b) allowing the reporter molecule to react with the pre-formed substrate to form a detectable reaction; and
(c) detecting the reaction.

19. The biosensor according to claim 10, wherein the means for measuring the activity of the reporter molecule in the cell is an instrument capable of measuring light output of the cells.

20. The biosensor according to claim 19, wherein the instrument capable of measuring the light output of the cells is selected from the group consisting of photomultiplier, charge coupled devices, luminometers, photometers, fiber-optic cables, and liquid scintillation counters.

* * * * *